US010160990B2

(12) United States Patent
Jalenques

(10) Patent No.: US 10,160,990 B2
(45) Date of Patent: Dec. 25, 2018

(54) ANALYSIS BAG, MANUFACTURING PROCESS FOR ANALYSIS BAGS, AND MICROBIAL CULTURE PROCESS USING THE SAME

(71) Applicant: Interscience, St Nom la Breteche (FR)

(72) Inventor: Emmanuel Jalenques, St Nom la Breteche (FR)

(73) Assignee: INTERSCIENCE, St Nom la Brèteche (FR)

( * ) Notice: Subject to any disclaimer, the term of this patent is extended or adjusted under 35 U.S.C. 154(b) by 160 days.

(21) Appl. No.: 15/043,947

(22) Filed: Feb. 15, 2016

(65) Prior Publication Data
US 2016/0237468 A1 Aug. 18, 2016

(30) Foreign Application Priority Data
Feb. 16, 2015 (FR) ...................................... 15 51256

(51) Int. Cl.
C12Q 1/02 (2006.01)
C12M 1/00 (2006.01)
B01L 3/00 (2006.01)

(52) U.S. Cl.
CPC ................ C12Q 1/02 (2013.01); B01L 3/505 (2013.01); C12M 23/14 (2013.01); B01L 2200/16 (2013.01); B01L 2300/069 (2013.01)

(58) Field of Classification Search
CPC ..... C12Q 1/02; B01L 3/505; B01L 2300/069; B01L 2200/16; C12M 23/14
See application file for complete search history.

(56) References Cited

U.S. PATENT DOCUMENTS

| | | | | | |
|---|---|---|---|---|---|
| 5,603,729 | A | * | 2/1997 | Brown | A61F 7/03 607/114 |
| 5,728,542 | A | * | 3/1998 | Charm | C12Q 1/06 422/28 |
| 6,146,875 | A | * | 11/2000 | Ward | C12M 23/14 383/104 |
| 6,176,371 | B1 | * | 1/2001 | Tyrrell | B01L 3/505 206/204 |
| 7,382,823 | B1 | * | 6/2008 | Cory | H04L 5/14 375/220 |
| 7,682,823 | B1 | * | 3/2010 | Runyon | C12M 23/14 210/616 |
| 9,163,208 | B2 | * | 10/2015 | Runyon | C12M 23/14 |

(Continued)

Primary Examiner — Michael L Hobbs
(74) Attorney, Agent, or Firm — Thomas P. O'Connell; O'Connell Law Firm

(57) ABSTRACT

An analysis bag for receiving a biological sample for microbial culture with a culture broth powder disposed within an inner volume of the container and retained by a porous wall. The culture broth powder can be disposed in at least one pouch comprising an envelope of porous material with an open inner volume. The container can have two compartments sharing a common porous wall with one compartment adapted to receive the culture broth powder and the other compartment adapted to receive the biological sample. The pouch can be manufactured with a panel of porous material folded over and sealed with the culture broth powder retained therein. A microbial culture process can be implemented with such analysis bags retaining at least one pouch or having compartments separated by a common porous wall.

17 Claims, 5 Drawing Sheets

(56) References Cited

U.S. PATENT DOCUMENTS

| | | | |
|---|---|---|---|
| 2005/0287512 A1* | 12/2005 | Cullis | A01N 1/02 435/1.3 |
| 2006/0054557 A1* | 3/2006 | Hori | A61M 1/3636 210/645 |
| 2007/0122894 A1* | 5/2007 | Richardson Casella | C12M 23/14 435/253.6 |
| 2012/0238011 A1* | 9/2012 | Tuohey | C12M 23/26 435/297.1 |
| 2016/0177245 A1* | 6/2016 | Johnson | C12M 23/14 435/401 |
| 2018/0087997 A1* | 3/2018 | Thenard | G01M 3/027 |
| 2018/0127797 A1* | 5/2018 | Brutinel | C12M 1/34 |

\* cited by examiner

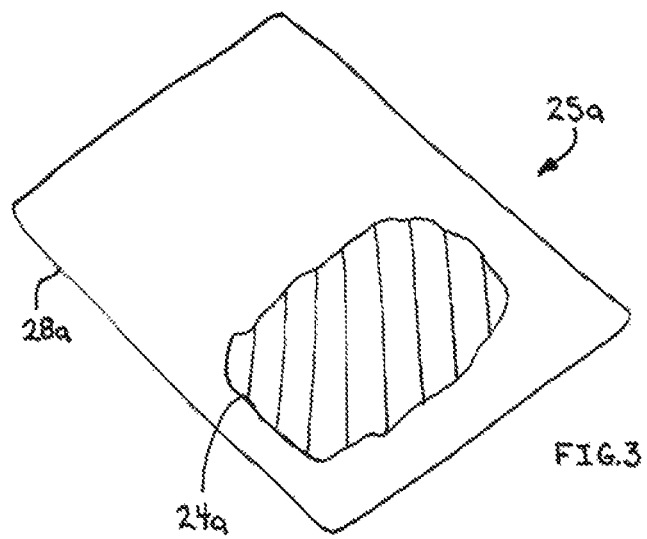
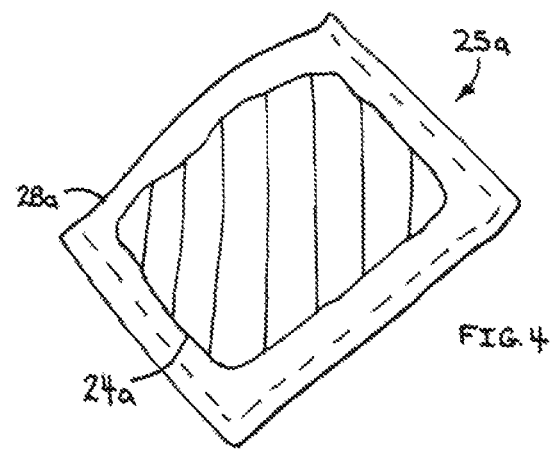

ND MICROBIAL CULTURE PROCESS USING
ANALYSIS BAG, MANUFACTURING PROCESS FOR ANALYSIS BAGS, AND MICROBIAL CULTURE PROCESS USING THE SAME

RELATED APPLICATION

This application claims priority to French Application No. 15 51256, filed Feb. 16, 2015.

FIELD OF THE INVENTION

The present invention relates generally to the field of microbial cultivation. More particularly, disclosed herein is an analysis bag for biological samples, to an analysis bag equipped with a pouch, to the manufacturing processes of such bags and pouches, and to the use of such bags during a microbial cultivation process.

BACKGROUND OF THE INVENTION

Microbial cultivation is a laboratory technique allowing controlled development of microorganisms, in-vitro growth, usually from a unique bacterial strain. Such cultivation eases the study of bacterial strains.

A culture medium is a medium that allows cultivating cells, bacteria, yeasts or molds to render their analysis possible. In principal, cells find in this medium the mandatory components needed to multiply in great number quickly but also sometimes elements that favor one bacterial genus or family. Thus, depending on the purpose of the culture, it is possible, for example, to place microorganisms under optimum development conditions or to do the complete opposite.

A culture medium is typically composed of a base such as agar, water, minerals, and a PH or redox indicator dye that allows raising a hypothesis on the genus. Some culture broths have the same function but do not contain agar and are thus fully liquid.

Broths conditioned as bottle or pouches are known. However, transportation of such bottles and pouches are a financial expense for their user. Bottles and pouches are voluminous, substantial in weight, and difficult to store. They also have a quite a short duration until expiration. A bottle or a pouch, once opened, must be used within the next 48 hours to avoid contamination. Another drawback of such packaging is the complicated manipulation that causes musculoskeletal disorders.

It is also known to have culture broths conditioned as powder. Such culture broths are normally reconstituted by mixing the powder with sterilized water and heating and shaking it. The reconstitution process is time consuming and is one drawback of such packaging. It takes several manipulations to craft, distribute, and sterilize it. Moreover, that type of packaging sometimes involves the use of thermally sensitive products, such as Half Fraser, so that the sterility of the operation in adding these products must also be ensured. Time-consuming and requiring multiple steps, the reconstitution process is normally limited to large capacity bottles or high volume containers, which are difficult to manipulate thereby risking musculoskeletal disorders.

In view of the foregoing, there is an apparent need for culture broth packaging that provides a solution to one or more of the aforementioned drawbacks. For example, the present inventor has appreciated that it would be useful to provide culture broth packaging that does not require the implementation of time-consuming steps and that involves fewer manipulations as are demanded by the prior art. It would also be advantageous to provide culture broth packaging capable of exhibiting a smaller size with concomitantly reduced storage and transportation costs and reduced risks of triggering or worsening musculoskeletal disorders. Still further, the present inventor has realized that providing a culture broth packaging that demonstrates a longer term until expiration would be a useful advance in the art.

SUMMARY OF THE INVENTION

The present invention thus has a basic object of providing culture broth packaging and a method for microbial culture processing using such culture broth packaging that presents a useful solution to one or more of the shortcomings of the prior art. A more particular object of embodiments of the invention is to provide culture broth packaging that limits the steps involved in its use thereby reducing the time required and necessitating fewer manipulations. Another object of embodiments of the invention is to provide culture broth packaging that exhibits reduced size thereby reducing storage and transportation costs and limiting the risks of triggering or worsening musculoskeletal disorders. Another object of manifestations of the culture broth packaging is to provide a longer term until expiration thereby, for example, reducing loss and risk of contamination.

In carrying forth one or more objects of the invention, an analysis bag is provided to receive a biological sample and to be implemented in microbial culturing. The analysis bag contains culture broth powder, which is able to be reconstituted to a culture broth when mixed with liquid, such as sterile water. The solution so obtained can then be homogenized, such as by use of a beater, a laboratory mixer, or another homogenization system. The analysis bag can be used in, for example, a laboratory mixer to perform bacterial extractions of a biological sample.

In certain embodiments, the culture broth powder can be delineated by at least a pouch. The pouch can have a porous interface allowing water circulation while retaining the powder. The pouch could be made of a non-woven material. The pouch could, in particular manifestations, have a thickness of approximately 150 µm, The pouch could have a porosity effective to permit the aforementioned water circulation and powder retention. The porosity could, by way of particular instance but not limitation, comprise openings in the pouch of approximately 10 µm. Embodiments of the pouch could have an areal density of approximately 10 g/m2.

Embodiments of the analysis bag could have one or more of the four aforementioned features of material, thickness, porosity, and areal density. Certain embodiments could have a combination of at least two of the four aforementioned features while other embodiments of the analysis bag could have three or even four of the features combined.

Embodiments of the analysis bag are contemplated wherein two compartments share a common porous wall. The first compartment can receive the culture broth powder, and the second compartment can receive the biological sample. The culture broth powder can be contained in a pouch with an envelope made of a water-soluble film. Embodiments are also contemplated wherein the pouch envelope is made of a film with a predetermined rupture area.

The analysis bag containing the culture broth powder can be sterilized. In particular embodiments, the analysis bag can be bagged in a plastic sheath and sterilized.

Also according to the invention, a pouch can be provided to be inserted in the analysis bag. The pouch can contain or receive a culture broth powder. In preferred embodiments, the pouch can be composed of a folded porous material welded to retain the culture broth powder inside.

Further disclosed herein is a manufacturing process for the pouch as taught herein, potentially from a sheet of a porous material. Practices of the pouch fabrication process can comprise the following steps:

Disposing culture broth powder on an area of the sheet of porous material; and

Folding the sheet, such as in half, and welding three edges of the folded sheet to retain the culture broth powder in the pouch so formed.

Additionally disclosed is a manufacturing process of an analysis bag according to the invention. This manufacturing process can, for example, comprise:

An insertion step during which the culture broth powder is inserted in the analysis bag;

A bagging step during which the analysis bag obtained previously is bagged in a plastic sheath;

A sterilization step during which the analysis bag obtained previously is sterilized.

The sterilization step could be implemented by a radio sterilization process. Under that process, radiation can be exploited to destroy, such as by cold, all types of microorganisms, bacteria, molds, etc. With that, the analysis bag can be used in relation to pharmaceutical and food packaging, industrial enzymes, cosmetics, etc.

Advantageously and when the analysis bag comprises a compartment fit to receive the culture broth powder, the process can include a step where the compartment is closed, such as by use of a porous wall. The step of closing the compartment can be implemented after the culture broth powder insertion step. It is further contemplated that the culture brother powder insertion step can be performed by inserting at least one pouch according to the invention.

A microbial culture process is proposed with the use of an analysis bag according to the invention. The microbial culture process can include a step whereing sterilized water is poured in the analysis bag after the culture broth has been inserted in the bag. This can be before or after biological insertion in the analysis bag.

One will appreciate that the foregoing discussion broadly outlines certain more important goals and features of the invention to enable a better understanding of the detailed description that follows and to instill a better appreciation of the inventor's contribution to the art. Before any particular embodiment or aspect thereof is explained in detail, it must be made clear that the following details of construction and illustrations of inventive concepts are mere examples of the many possible manifestations of the invention. It will thus be clear that additional features and benefits of the invention will be apparent through a reading of the detailed description of implementations and embodiments, which are without restriction, and by reference to the attached figures.

BRIEF DESCRIPTION OF DRAWINGS

Additional features and benefits of the analysis bag for biological samples, analysis bags equipped with pouches, manufacturing processes of such bags and pouches, and the microbial cultivation process using such bags will be apparent to one skilled in the art after reviewing the present specification and drawings, wherein:

FIG. 3 is a perspective view of a pouch retaining a volume of culture broth powder during a step in a process of manufacturing thereof;

FIG. 4 is a perspective view of a pouch retaining a volume of culture broth powder during a later step in a process of manufacturing thereof;

DETAILED DESCRIPTION OF PREFERRED EMBODIMENTS

The analysis bag for biological samples, analysis bags equipped with pouches, manufacturing processes of such bags and pouches, and the microbial cultivation process using such bags disclosed herein are subject to varied embodiments. However, to ensure that one skilled in the art will be able to understand and, in appropriate cases, practice the present invention, certain preferred embodiments of the broader invention revealed herein are described below and shown in the accompanying drawing figures. Therefore, before any particular embodiment of the invention is explained in detail, it must be made clear that the following details of construction and illustrations of inventive concepts are mere examples of the many possible manifestations of the invention.

Figure 1:
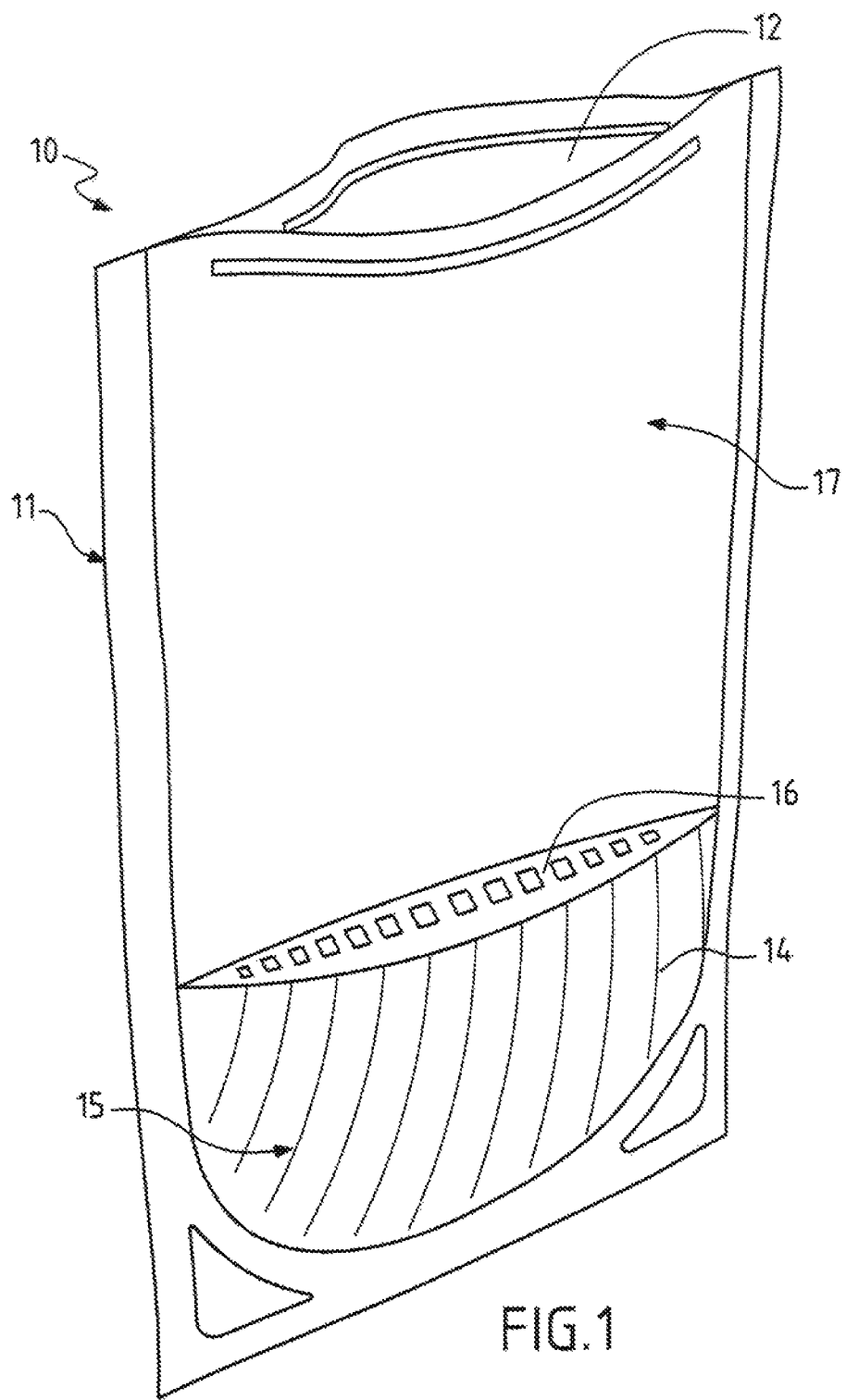
FIG. 1 is a schematic, perspective view of an analysis bag according to the invention.

With this in mind and looking more particularly to the accompanying figures, an embodiment of the analysis bag disclosed herein is indicated generally at 10 in FIG. 1. The analysis bag 10 is founded on a container 11 for the microbial culturing of a biological sample. In certain embodiments, the container 11 can have first and second, opposed container walls. The walls can be sealed along three edges to form a bag. The container 11 can, in certain embodiments, be formed from a polymeric film. The edges of the walls could be sealed by any suitable method and any material or combination of materials to cause the bottom and lateral edges of the walls to be sealed. The container 11 has an opening 12 along which the first and second container walls are not mutually sealed. The opening 12 can be selectively closed.

The opening 12 permits the introduction of a biological sample into the inner volume defined by the first and second walls of the container 11. A culture broth powder 14, represented as a hatched area in FIG. 1, can thus be disposed in the inner volume of the container 11.

A sub-compartment 15 with an inner volume is disposed within the inner volume of the container 11. The inner volume of the sub-compartment 15 can, for instance, be separated from the inner volume of the container 11 exterior to the sub-compartment 15 by a wall, which is schematically indicated at 16. The wall 16 can be a porous wall 16 with that porosity schematically indicated by the squares in the wall 16 in FIG. 1. The sub-compartment 15 so formed is bounded laterally by the first and second walls and sealed side portions thereof, proximally by the sealed bottom portions of the walls, and distally by the porous wall 16.

The porous wall 16 thus divides the container 11 in two volumes or compartments, which can be characterized as the sub-compartment 15 proximal to the porous wall 16 and a main compartment 17 distal to the porous wall 16. The compartments 15 and 17 share a common wall, namely the porous wall 16. The first compartment 15 is adapted to receive the culture broth powder 14, and the second compartment 17 is adapted to receive the biological sample.

Figure 5:
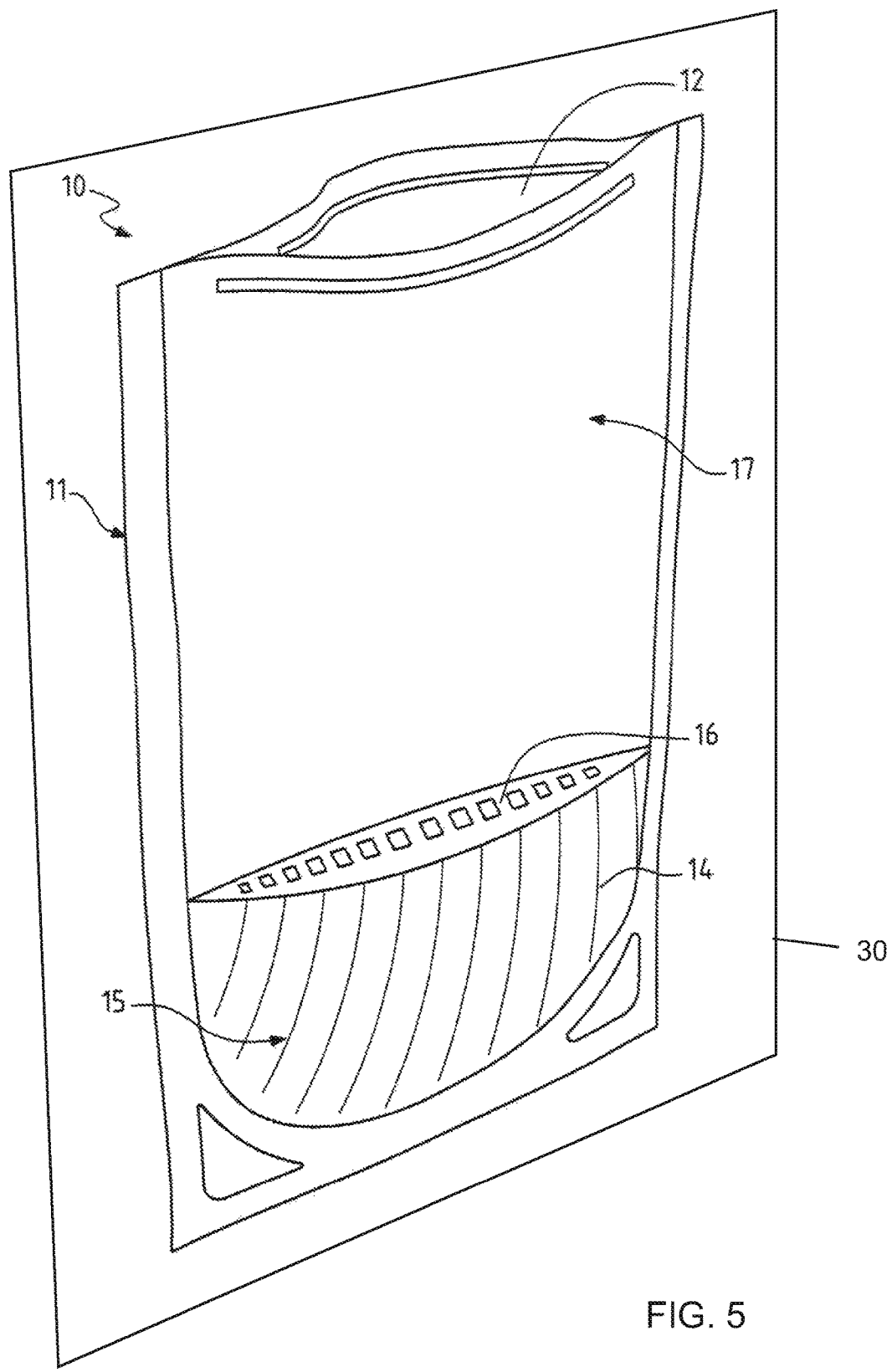
FIG. 5 is a schematic, perspective view of the analysis bag of FIG. 1 enveloped in a plastic sheath.

Under certain practices of the invention, an analysis bag 10 according to the invention could be founded on a pre-existing analysis bag according to the prior art. Such a manufacturing process could include an insertion step during which culture broth powder 14 is inserted into the inner volume of the analysis bag. A bagging step can then be undertaken during which the analysis bag is wrapped in a plastic sheath 30 as shown, for instance, in FIG. 5. Then, a sterilization step can be performed of the analysis bag 10 so wrapped in a plastic sheath 30. The manufacturing process of the analysis bag 10 can further comprise a step of closing off the first compartment 15, such as by the porous wall 16. The step of closing off can be implemented after the culture broth powder insertion step.

The analysis bag 10 so formed can be used to practice an ingenious method for microbial culturing. According to the invention, microbial culturing can be performed with an additional step, subsequent to the insertion of the culture broth powder 14 in the analysis bag 10, during which sterile water is added. With this, depending on the weight of the sample to be analyzed, it is possible to choose an analysis bag 10 containing an appropriate mass of culture broth 14 and to add the necessary volume of sterile water to it. The greater the weight of the sample to be analyzed, the greater the mass of the selected culture broth 14.

By way of example and not limitation, if 25 grams of biological sample have to be analyzed, one may use a culture broth that comprises 5.7 grams of buffered peptonized water in powder or 2.1 grams of tryptone salt in powder or 13 grams of enriched Half Fraser in powder. Such a culture broth can be reconstituted by adding 225 milliliters of sterilized water. If, for example, 10 grams of biological sample have to be analyzed, one may use a culture broth that comprises 2.3 grams of buffered peptonized water in powder or 0.9 grams of tryptone salt in powder or 5.2 grams of enriched Half Fraser in powder. Such a culture broth can be reconstituted by adding 90 milliliters of sterilized water.

Thus, it is possible to use different masses of various culture broth powders 14 depending on the weight of the sample that has to be analyzed The volume of sterilized water that has to be added could remain identical. Once introduced into the inner volume of the container 11, the culture medium can then be used for the microbial culture of the biological sample inside container 11.

Figure 2:
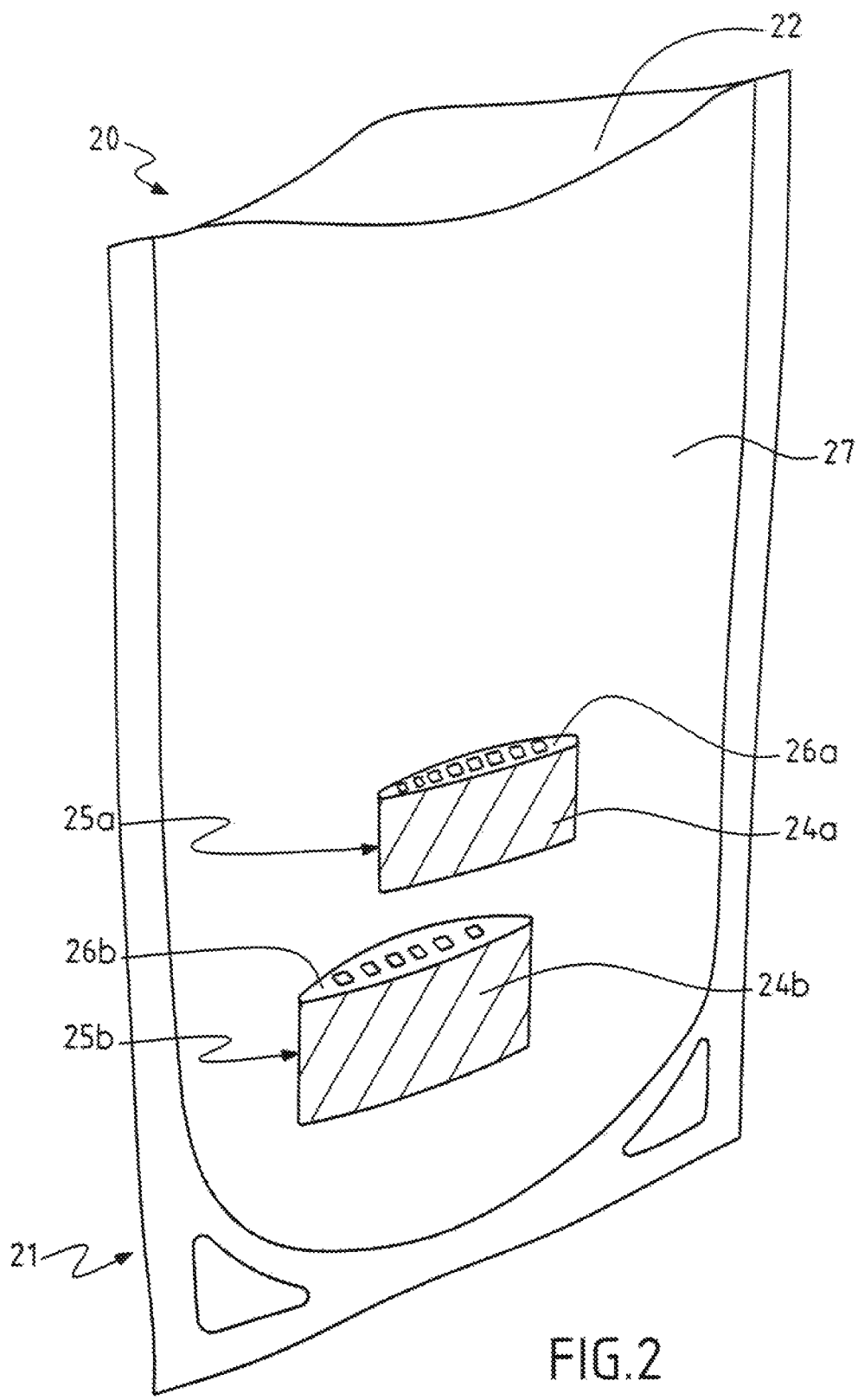
FIG. 2 is a schematic, perspective view of an alternative analysis bag as disclosed herein.

An alternative embodiment of the analysis bag 20 according to the invention is indicated generally at 20 in FIG. 2. There, the analysis bag 20 is founded on a container 21 for the microbial culturing of a biological sample. The container 21 has first and second, opposed container walls. The walls are sealed along three edges to form a bag. The container 21 can be formed from a polymeric film or any other suitable material fit for microbial culturing and so that the container 21 has sufficient physical characteristics to be leak-tight. The edges of the walls could be sealed by any suitable method and any material or combination of materials to cause the bottom and lateral edges of the walls to be sealed. The container 21 has an opening 22 along which the first and second container walls are not mutually sealed. The opening 22 permits the introduction of a biological sample into the inner volume defined by the first and second walls of the container 21.

The analysis bag 20 retains volumes of culture broth powder 24*a*, 24*b*, which are displayed as hatched areas in FIG. 2. The volumes of culture broth powder 24*a*, 24*b* in this embodiment are retained by two pouches, 25*a*, 25*b* respectively. Pouch 25*a* has a porous interface 26*a*, and pouch 25*b* has a porous interface 26*b*. The porous interfaces 26*a*, 26*b* are illustrated as squares within the pouches 25*a*, 25*b* in FIG. 2, but their depiction is schematic and should not be interpreted as limiting.

The pouches 25*a*, 25*b* themselves can be made of a porous material. They could, for instance, comprise a panel of material folded over and welded over the edges thereof so that the culture broth powder 24*a*, 24*b* is respectively retained in pouches 25*a*, 25*b*.

The porous walls 26*a*, 26*b* divide the contents of the two pouches 25*a*, 25*b* from one another and from the volume 27 of the container 21 exterior to the pouches 25*a*, 25*b*. The culture broth powder 24*a*, 24*b* is thus retained within the respective pouches 25*a*, 25*b*. The volume of the container 21 exterior to the pouches 25*a*, 25*b* is thus fit to receive a biological sample.

With further reference to FIGS. 3 and 4 where pouch 25*a* is depicted in stages of manufacture, each pouch 25*a*, 25*b* could be made from a sheet of a porous material, referenced at 28*a* for pouch 25*a*, in a manufacturing process wherein culture broth powder 24*a*, 24*b* respectively is placed on a zone of the sheet 28*a*. Then, the sheet 28*a* can be folded, such as in half as in FIG. 4. With the sheet 28*a* so folded, the three open sides thereof can be sealed, such as by thermo welding, ultrasonic welding, or any other known method. The pouches 25*a*, 25*b* thus comprise envelopes with inner volumes. With that, the culture broth powder 24*a*, 24*b* is retained in the pouch 25*a*, 25*b* crafted this way.

Figure 6:
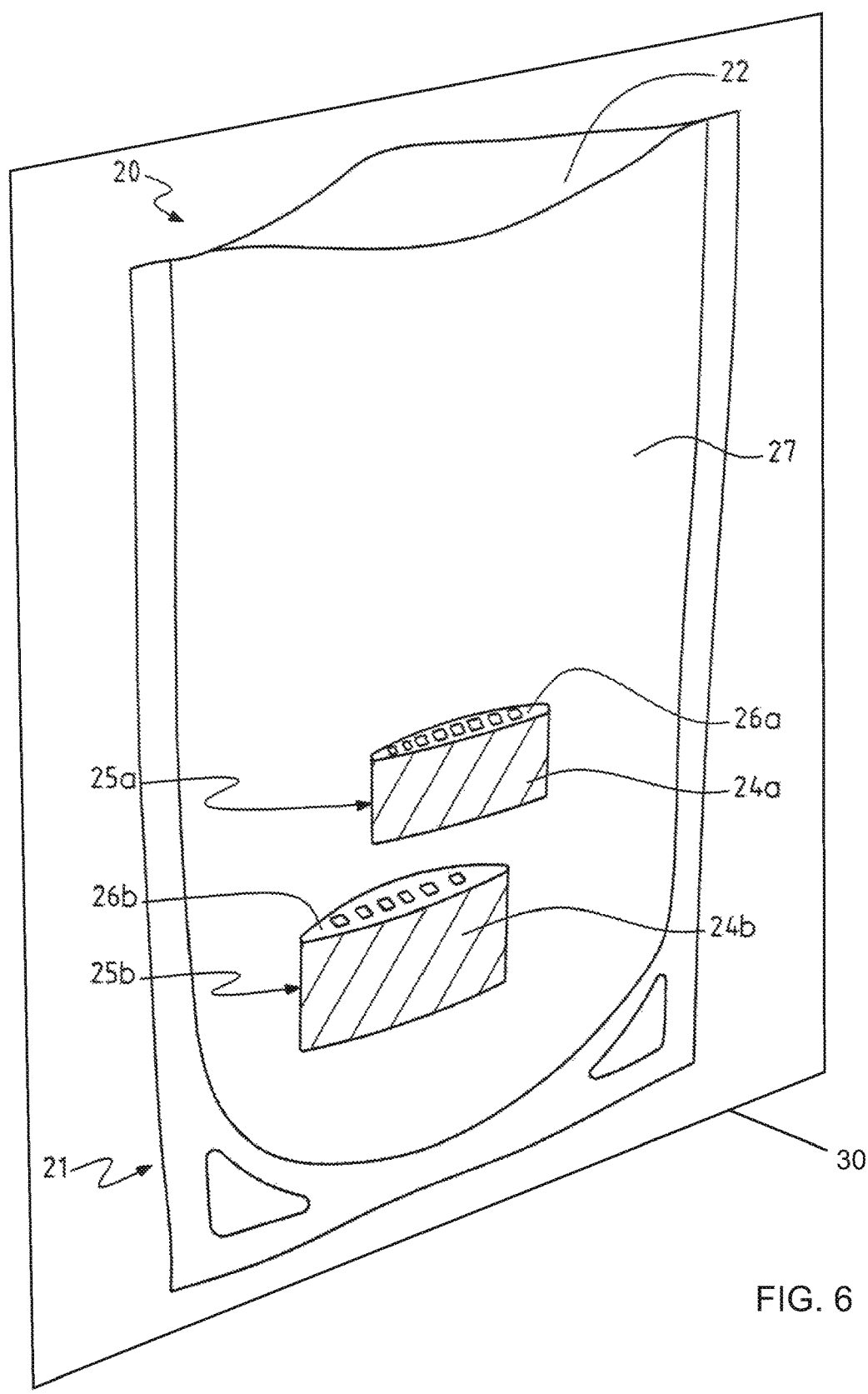
FIG. 6 is a schematic, perspective view of the analysis bag of FIG. 2 enveloped in a plastic sheath.

By use of one or more of the pouches 24*a*, 24*b* so disclosed, an analysis bag 20 according to the invention could be founded on a pre-existing analysis bag according to the prior art. Such a manufacturing process could include an insertion step during which culture broth powder 24*a*, 24*b* is inserted into the analysis bag container 21 by inserting at least one pouch 25*a* or 25*b* retaining the culture broth powder 24*a*, 24*b* as described above. A bagging step can then be undertaken during which the analysis bag 20 obtained previously is wrapped in a plastic sheath 30 as shown, for instance, in FIG. 6. Then, a sterilization step can be performed of the analysis bag 20 so wrapped in a plastic sheath 30.

The analysis bag 20 so formed can be used to practice an ingenious method for microbial culturing. In fact, and according to the invention, microbial culture using such an analysis bag comprises a step during which sterile water is added after the pouches 25*a*, 25*b* were inserted in the analysis bag 20 while both containing culture broth powder 24*a*, 24*b*.

Thus, depending on the weight of the biological sample to be analyzed, it is possible to choose an analysis bag 20 that contains the appropriate mass of culture broth and to add the necessary volume of sterilized water to it. For example, if 25 grams of biological sample are to be analyzed, one might use a culture broth pouch 25*a*, 25*b* containing 5.7 grams of buffered peptonized water in powder or a culture broth pouch 25*a*, 25*b* containing 2.1 grams of tryptone salt in powder or a culture broth pouch 25*a*, 25*b* containing 13 grams of enriched Half Fraser in powder. The contents of any of the three pouches 25*a*, 25*b*, once diluted by adding 225 milliliters of sterilized water, constitutes the culture broth used for the analysis of the biological sample. If 10 grams of biological sample are to be analyzed, one might use a culture broth pouch 25*a*, 25*b* containing 2.3 grams of buffered peptonized water in powder or a culture broth pouch 25*a*, 25*b* containing 0.9 grams of tryptone salt in powder or a culture broth pouch 25*a*, 25*b* containing 5.2 grams of enriched Half Fraser in powder. The contents of any of the pouches 25a, 25b, once diluted by adding 90 milliliters of sterilized water, constitutes the culture broth used for the analysis of the biological sample. It is thus possible to use, depending on the sample weight and the type of analysis to be performed, different masses of various culture broth powders while the volume of sterilized water that has to be added to it can remain unchanged. Once introduced inside the container 21, the culture medium is used for microbial culture of the biological sample inside the container 21.

With certain details and embodiments of the present invention for an analysis bag for biological samples, analysis bags equipped with pouches, manufacturing processes of such bags and pouches, and the microbial cultivation process using such bags disclosed, it will be appreciated by one skilled in the art that numerous changes and additions could be made thereto without deviating from the spirit or scope of the invention. This is particularly true when one bears in mind that the presently preferred embodiments merely exemplify the broader invention revealed herein. Accordingly, it will be clear that those with major features of the invention in mind could craft embodiments that incorporate those major features while not incorporating all of the features included in the preferred embodiments.

Therefore, the following claims are intended to define the scope of protection to be afforded to the inventor. Those claims shall be deemed to include equivalent constructions insofar as they do not depart from the spirit and scope of the invention. It must be further noted that a plurality of the following claims may express certain elements as means for performing a specific function, at times without the recital of structure or material. As the law demands, these claims shall be construed to cover not only the corresponding structure and material expressly described in this specification but also equivalents thereof.

I claim as deserving the protection of Letters Patent:

1. An analysis bag for receiving a biological sample for microbial culture, wherein the analysis bag comprises:
   a container with an inner volume wherein the inner volume of the container is separated into a sub-compartment and a main compartment by a common porous wall shared by the main compartment and the sub-compartment; and
   a culture broth powder retained within the sub-compartment and sealed from the main compartment by the porous wall;
   wherein the porous wall has a porosity comprising openings in the porous wall effective to retain the culture broth powder within the sub-compartment and effective to permit a circulation of water through the porous wall and into the sub-compartment.

2. The analysis bag of claim 1 wherein the culture broth powder comprises buffered peptonized water in powder, tryptone salt in powder, or enriched Half Fraser in powder.

3. The analysis bag of claim 1 wherein the container has a first and second, opposed container walls sealed along edges of the first and second, opposed container walls wherein the sub-compartment is bounded by the first and second, opposed container walls and the porous wall.

4. The analysis bag of claim 3 wherein the analysis bag is sterile.

5. The analysis bag of claim 1 wherein the porous wall has a porosity formed by openings of approximately 10 µm in the porous wall.

6. An analysis bag for receiving a biological sample for microbial culture, wherein the analysis bag comprises:
   a container with an inner volume wherein the inner volume of the container has a main compartment;
   a pouch with an inner volume wherein the pouch comprises an envelope of porous material; and
   a volume of culture broth powder disposed within the inner volume of the pouch;
   wherein the porous wall has a porosity comprising openings in the porous wall effective to retain the culture broth powder within the sub-compartment and effective to permit a circulation of water through the porous wall and into the sub-compartment.

7. The analysis bag of claim 6 wherein the culture broth powder comprises buffered peptonized water in powder, tryptone salt in powder, or enriched Half Fraser in powder.

8. A manufacturing process for a pouch retaining a volume of culture broth powder, the process comprising the following steps:
   providing a panel of porous material, the panel of porous material forming a porous wall wherein the porous wall has a porosity comprising openings in the porous wall;
   placing a volume of culture broth powder on a zone of the panel;
   folding the panel over to cause three sides to overlap; and
   sealing the three sides whereby an envelope with an open inner volume is formed with the culture broth powder retained in the open inner volume.

9. A manufacturing process for an analysis bag, the process comprising the following steps:
   providing an analysis bag for receiving a biological sample for microbial culture wherein the analysis bag comprises a container with an inner volume;
   an insertion step comprising inserting a dose of culture broth powder into the inner volume of the analysis bag wherein the insertion step comprises disposing the culture broth powder to be retained by a porous wall that has a porosity comprising openings in the porous wall;
   a bagging step during which the analysis bag with the dose of culture broth powder disposed therein is wrapped in a plastic sheath; and
   a sterilization step of the analysis bag wrapped in a plastic sheath.

10. The manufacturing process of claim 9 wherein the sterilization step is performed by radio sterilization.

11. The manufacturing process of claim 9 further comprising a closing step wherein the container has first and second, opposed container walls sealed along edges of the first and second, opposed container walls and wherein the container is separated into two compartments by the porous wall in the closing step wherein the closing step is performed after the insertion step.

12. The manufacturing process of claim 9 wherein the insertion step of the culture broth powder is performed by inserting at least one pouch with an inner volume wherein the pouch retains a volume of culture broth powder and wherein the pouch is defined by the porous wall.

13. The manufacturing process of claim 12 wherein the pouch comprises an envelope of porous material with an inner volume and wherein the volume of culture broth powder is disposed in the inner volume of the envelope.

14. The manufacturing process of claim 11 wherein the closing step comprises disposing the porous wall to separate the inner volume of the analysis bag into two compartments with the porous wall comprising a common porous wall shared by the two compartments with one of the two compartments comprising a sub-compartment into which the culture broth powder is inserted and the other of the two compartments comprises a main compartment adapted to receive the biological sample, and wherein the sub-compartment is bounded by the first and second, opposed container walls and the porous wall.

15. A microbial culture process, the microbial culture process comprising the following steps:
   providing an analysis bag for receiving a biological sample for microbial culture, the analysis bag comprising a container with an inner volume and a culture broth powder disposed within the inner volume of the container wherein the culture broth powder is retained within the inner volume of the container by a porous wall wherein the porous wall has a porosity comprising openings in the porous wall;
   disposing a biological sample in the inner volume of the container; and
   adding water to the inner volume of the container.

16. The microbial culture process of claim 15 wherein the culture broth powder is disposed in at least one pouch, wherein the pouch is defined by the porous wall and wherein the pouch is disposed within the inner volume of the container.

17. The microbial culture process of claim 15 wherein the container has first and second, opposed container walls sealed along edges of the first and second, opposed container walls and wherein the container is separated into two compartments by the porous wall, wherein the porous wall comprises a common porous wall shared by the two compartments, wherein one of the two compartments comprises a sub-compartment adapted to receive the culture broth powder and the other of the two compartments comprises a main compartment adapted to receive the biological sample, and wherein the sub-compartment is bounded by the first and second, opposed container walls and the porous wall.

* * * * *